(12) United States Patent
Zhou et al.

(10) Patent No.: US 8,710,094 B2
(45) Date of Patent: Apr. 29, 2014

(54) QUINOID THIOPHENE ORGANIC PHOTOELECTRIC MATERIAL, PREPARATION METHOD THEREOF AND APPLICATION THEREOF

(75) Inventors: Mingjie Zhou, Guangdong (CN); Jie Huang, Guangdong (CN); Hui Liu, Guangdong (CN)

(73) Assignee: Ocean's King Lighting Science & Technology Co., Ltd., Guangdong (CN)

( * ) Notice: Subject to any disclaimer, the term of this patent is extended or adjusted under 35 U.S.C. 154(b) by 79 days.

(21) Appl. No.: 13/575,648

(22) PCT Filed: Jan. 30, 2010

(86) PCT No.: PCT/CN2010/070436
§ 371 (c)(1),
(2), (4) Date: Jul. 27, 2012

(87) PCT Pub. No.: WO2011/091608
PCT Pub. Date: Aug. 4, 2011

(65) Prior Publication Data
US 2012/0302763 A1    Nov. 29, 2012

(51) Int. Cl.
*A61K 31/381* (2006.01)
*C07D 333/50* (2006.01)

(52) U.S. Cl.
USPC .................................. 514/443; 549/41

(58) Field of Classification Search
USPC .................................. 514/443; 549/41
See application file for complete search history.

(56) References Cited

FOREIGN PATENT DOCUMENTS

| CN | 1706848 A | 12/2005 |
|---|---|---|
| EP | 2068379 A1 | 6/2009 |
| JP | 2007-211174 A | 8/2007 |
| JP | 2009-275003 A | 11/2009 |
| WO | 2008/032715 A1 | 3/2008 |

OTHER PUBLICATIONS

Gallazzi, et al.; "Polythiophenes with Unusual Electrical and Optical Properties Based on Donor Acceptor Alternance Strategy"; Macromol. Chem. Phys.; 2001, vol. 202, pp. 2074-2085.
Frey, et al.; "Improved synthesis of dithieno[3,2-b:2',3'-d]thiophene (DTT) and derivatives for cross coupling"; Chemical Communications; 2002, pp. 2424-2425.
Communication from the Chinese Patent Office regarding a counterpart foreign application dated Apr. 3, 2013.
Yui, et al.; "Novel electron acceptors bearing a heteroquinonoid system. I. Synthesis and conductive complexes of 5,5'-bis(dicyanomethylene)-5,5'-dihydro-Δ(2,2')-bithiophene and related compounds"; Bulletin of the Chemical Society of Japan, May 1989; vol. 62, No. 5; pp. 1539-1546.
Yui, et al.; "Novel electron acceptors bearing a heteroquinonoid system. II. Synthesis and conductive complexes of 2,5-bis(dicyanomethylene)-2,5-dihydrothieno-[3,2-b] thiophene, 2,6-bis(dicyanomethylene)-2,6-dihydrodithieno[3,2-b:2',3'-d]thiophene, and their derivatives"; Bulletin of the Chemical Society of Japan, May 1989; vol. 62, No. 5; pp. 1547-1555.
Communication from the Japanese Patent Office regarding a counterpart foreign application dated (Emperor Year 25) Sep. 19, 2013.
Yoshida, et al; "Novel Electron Acceptors Bearing a Heteroquinonoid System. 4. Syntheses, Properties, and Charge-Transfer Complexes of 2,7-Bis(dicyanomethylene)-2,7-dihydrobenzo[2,1-b:3,4-b']dithiophene, 2,7-Bis (dicyanomethylene)-2,7-dihydrobenzo[1,2-b:4,3-b']dithiophene, and 2,6-Bis(dicyanomethylene)-2,6-dihydrobenzo[1,2-b:4,5-b']dithiophene"; J. Org. Chem., 1994, 59 (11), pp. 3077-3081.
Communication From the European Patent Office Regarding a Counterpart Foreign Application Dated Jun. 6, 2013.

*Primary Examiner* — Taofiq A Solola
(74) *Attorney, Agent, or Firm* — Rosenberg, Klein & Lee

(57) ABSTRACT

Quinoid thiophene organic photoelectric material with formula (1), method for its preparation and application thereof are provided, wherein $R_1$, $R_2$, $R_3$, $R_4$, $R_5$ and $R_6$, which are identical or different, represent H, $C_1$~$C_{30}$ alkyl or alkoxy, m and n, which are identical or different, represent integers between 1 and 20. The quinoid thiophene organic photoelectric material with formula (1) has wide spectral response, good thermal stability and environmental stability.

13 Claims, 5 Drawing Sheets

QUINOID THIOPHENE ORGANIC PHOTOELECTRIC MATERIAL, PREPARATION METHOD THEREOF AND APPLICATION THEREOF

FIELD OF THE INVENTION

The present disclosure relates to organic materials technology, and more particularly relates to quinoid thiophene organic photoelectric material, preparation method thereof and application thereof.

BACKGROUND OF THE INVENTION

The current the world economy is built on the basis of fossil fuels, such as coal, oil and gas. However, these non-renewable fossil fuels are constantly depleting. Since the beginning of the 21st century, global energy issues, consequent environmental pollution and global warming become more apparent and gradually intensified. Solar energy is considered to be one of the most promising renewable energy, as it has widespread and broad distribution, high resource quantity, pollution-free, clean, safe and convenient access to the outstanding merits. Solar cells transform solar energy into electricity directly, and it is an effective method of using solar energy practical. However, the current commercialization solar cells are restricted to silicon and other inorganic solar cells, which are too expensive that beyond the acceptable level, and this limits their scope of application. In order to reduce the costs of battery and expand the application scope of battery, for a long time, people have been looking for a new type of solar cell materials.

Organic solar cell is a new type of solar cell, relative to the inorganic semiconductor materials which is limited sources, expensive, toxic, complex preparation, high cost, organic solar cell has some advantages, such as wide range of sources of materials, structural diversity and regulation, low cost, safety and environmental protection, simple preparation, light weight, flexible preparation of large area, and etc. Organic solar cell can be widely used in the field of architecture, lighting and power generation, and has important development and application prospects. Therefore, many domestic and international research institutions and enterprises are all given considerable attention and investment. So far, however, the photoelectric conversion efficiency of organic solar cell is much lower than inorganic solar cells. Therefore, the development of new organic optoelectronic materials has great significance for improving the efficiency of organic solar cells and other semiconductor devices.

SUMMARY OF THE INVENTION

In one aspect of the present disclosure, a quinoid thiophene organic photoelectric material with wide spectral response, good thermal stability and environmental stability is desired.

In another aspect of the present disclosure, a preparation method of the quinoid thiophene organic photoelectric material with simple operation and low cost is also desired.

Embodiments of the present disclosure also reveal that the quinoid thiophene organic photoelectric material can be used in manufacture of solar cell devices, organic field-effect transistors and organic electroluminescent devices, organic optical memory, non-linear organic materials or organic laser devices.

A quinoid thiophene organic photoelectric material, includes the compound represented by the following formula (1):

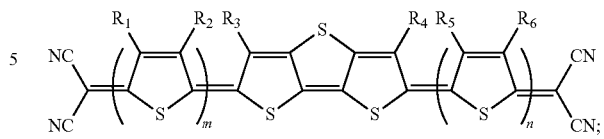

(1)

wherein $R_1$, $R_2$, $R_3$, $R_4$, $R_5$ and $R_6$, which are identical or different, represent H or $C_1$~$C_{30}$ alkyl or alkoxy, m and n, which are identical or different, represent integers between 1 and 20.

A preparation method of quinoid thiophene organic photoelectric material, includes:
compounds A, B, C represented by the following formulas and malononitrile is provided, respectively,

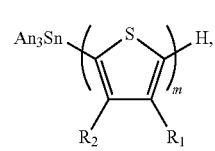

A

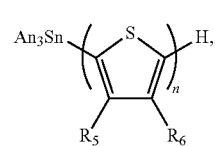

B

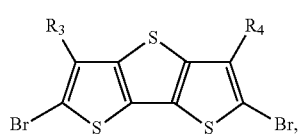

C wherein $R_1$, $R_2$, $R_3$, $R_4$, $R_5$ and $R_6$, which are identical or different, represent H or $C_1$~$C_{30}$ alkyl or alkoxy, m and n, which are identical or different, represent integers between 1 and 20, An represents $C_1$~$C_4$ alkyl;
compounds A, B, and C are processed by Stille coupling reaction in the presence of a catalyst and a solvent;
the product of Stille coupling reaction is processed by bromide substitution reaction to obtain a product of bromide substitution reaction;
the product of bromide substitution reaction and malononitrile are processed by condensation reaction in the presence of a catalyst, a condensing agent and a solvent to obtain the compound represented by the following formula (1):

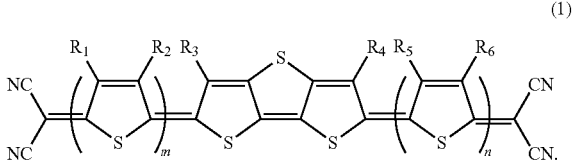

(1)

A method for the applications of the quinoid thiophene organic photoelectric material described above in manufacture of solar cell devices, organic field-effect transistors, organic electroluminescent devices, organic optical memory, non-linear organic materials or organic laser devices.

The quinoid thiophene organic photoelectric material described above has a plurality of thiophene rings with quinoid structures, and the thiophene ring is five-membered ring structure which complies with Huckel rule, having moderate energy bandgap, wide spectral response, good thermal stability and environmental stability. Moreover, the quinoid thiophene organic photoelectric material described above has strong electron withdrawing groups cyano vinyl ($=C(CN)_2$) at both ends of the molecular chain, that make it become quinoid thiophene containing dithiophene and thiophene unit, further widening the range of the material on the absorption of the solar spectrum, for example, push the absorption band edge of material to the red and near infrared region, to improve the optical and electrical properties of the material and the photoelectric conversion efficiency of the material. In the preparation method of quinoid thiophene organic photoelectric material described above, the use of relatively simple synthetic route and Stille coupling reactions simplifies the process and reduces manufacturing costs. While the quinoid thiophene organic photoelectric material described above is used in solar cell devices, organic field-effect transistors and organic electroluminescent devices, organic optical memory, non-linear organic materials or organic laser devices, their the optical or semiconductor-related performance can be improved, their quality can be reduced, and it can facilitate the preparation of large quantities.

BRIEF DESCRIPTION OF THE DRAWINGS

The components in the drawings are not necessarily drawn to scale, the emphasis instead being placed upon clearly illustrating the principles of the present disclosure.

DETAILED DESCRIPTION

In order to make the purpose, the technical solutions and benefits of the present disclosure more clearly, the present disclosure is detailed explained in the following embodiments with reference to the accompanying drawings. It should be understood that the following embodiments is only to explain the present disclosure, not used to limit the present disclosure.

Figure 1:
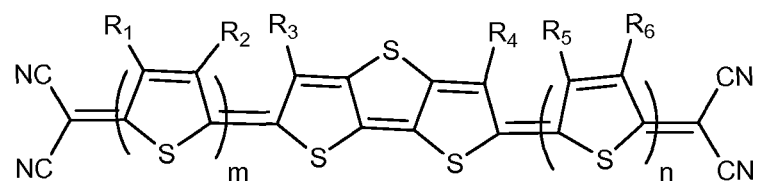
FIG. 1 is a schematic view of a quinoid thiophene organic photoelectric material represented by the formula (1) according to an embodiment of the present disclosure.

Referring to FIG. 1, an embodiment of quinoid thiophene organic photoelectric material with the formula (1), which includes the compound represented by the following formula (1):

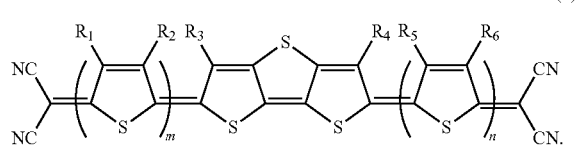

(1)

Wherein $R_1$, $R_2$, $R_3$, $R_4$, $R_5$ and $R_6$, which are identical or different, represent H or $C_1$~$C_{30}$ alkyl or alkoxy, m and n, which are identical or different, represent integers between 1 and 20.

In an embodiment of the present disclosure, the quinoid thiophene organic photoelectric material has a symmetrical molecular structure. For example, m and n are identical, that means m=n. In a preferred embodiment of the present disclosure, m=n=1 or m=n=2, in this case, the molecular weight of the quinoid thiophene organic photoelectric material is small, and the weight of product using the quinoid thiophene organic photoelectric material is light. In an embodiment of the present disclosure, $R_1$ and $R_6$, which are identical, represent H or $C_1$~$C_{30}$ alkyl or alkoxy, $R_2$ and $R_5$, which are identical, represent H or $C_1$~$C_{30}$ alkyl or alkoxy. $R_3$ and $R_4$, which are identical, represent H or $C_1$~$C_{30}$ alkyl or alkoxy. Such structure can simplify the preparation process and reduce production costs. In a preferred embodiment, $R_1$, $R_2$, $R_3$, $R_4$, $R_5$ and $R_6$ are H.

The quinoid thiophene organic photoelectric material described above has a plurality of thiophene rings with quinoid structures, and the thiophene ring is five-membered ring structure which complies with Huckel rule, having moderate energy bandgap, wide spectral response, and its absorption band is 300~700 nm which basically covers the visible light. In addition, the quinoid thiophene organic photoelectric material has good thermal stability, environmental stability, and exhibits good optical and electrical properties. Moreover, the quinoid thiophene organic photoelectric material described above has strong electron withdrawing groups cyano vinyl ($=C(CN)_2$) at both ends of the molecular chain, which make it become quinoid thiophene containing dithiophene and thiophene unit, further widening the range of the material on the absorption of the solar spectrum, for example, the absorption band edge of material is pushed to the red and near infrared region, such that the optical and electrical properties of the material and the photoelectric conversion efficiency of the material are improved.

Figure 2:
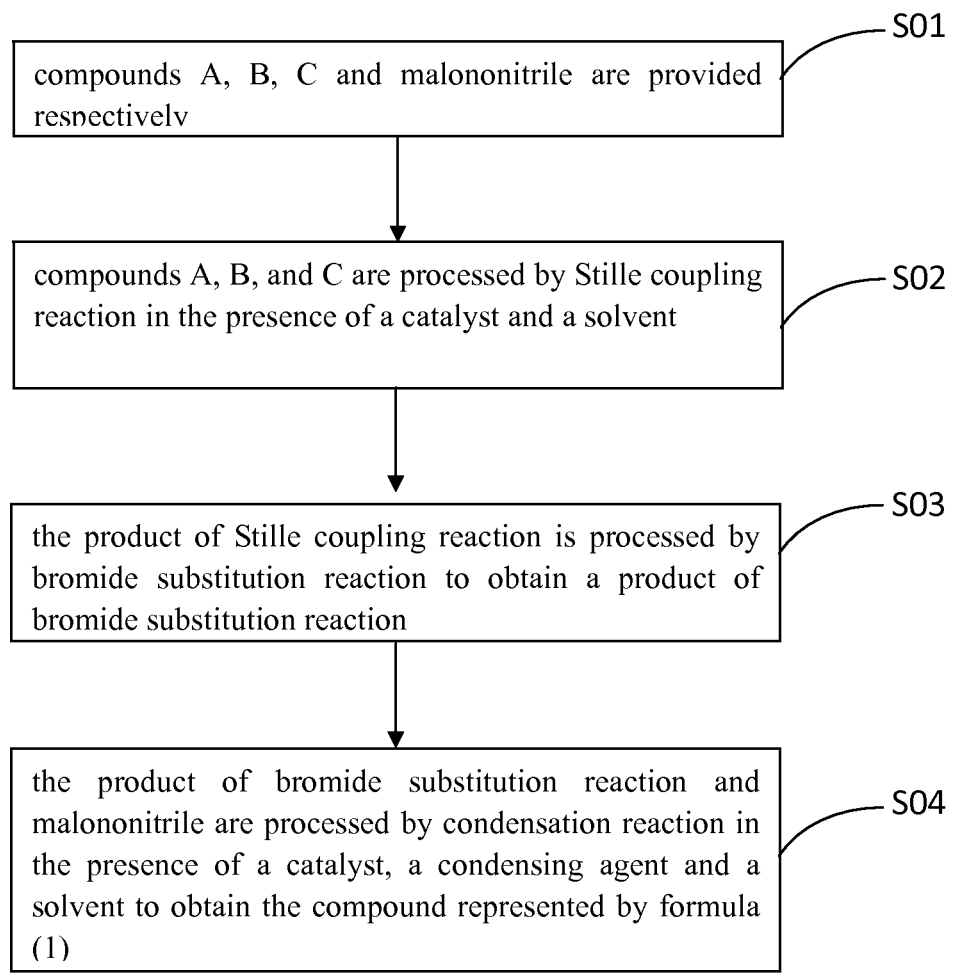
FIG. 2 is a flow chart of a preparation method of quinoid thiophene organic photoelectric material according to an embodiment of the present disclosure.

Referring to FIG. 2, the preparation method of quinoid thiophene organic photoelectric material described above includes following steps:

step 01: compounds A, B, C represented by the following formula and malononitrile are provided, respectively,

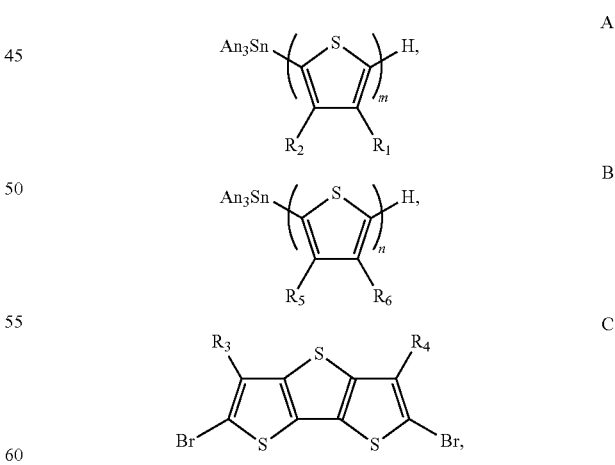

wherein $R_1$, $R_2$, $R_3$, $R_4$, $R_5$ and $R_6$, which are identical or different, represent H or $C_1$~$C_{30}$ alkyl or alkoxy, m and n, which are identical or different, represent integers between 1 and 20, An represents $C_1$~$C_4$ alkyl;

step 02, compounds A, B, and C are processed by Stille coupling reaction in the presence of a catalyst and a solvent;

step 03, the product of Stille coupling reaction are processed by bromide substitution reaction to obtain a product of bromide substitution reaction;

step 04, the product of bromide substitution reaction and malononitrile are processed by condensation reaction in the presence of a catalyst, a condensing agent and a solvent to obtain the compound represented by the following formula (1):

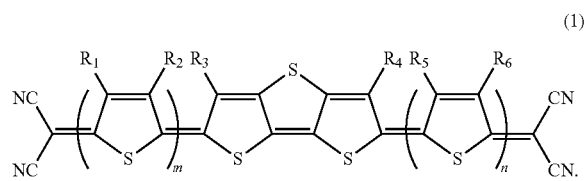

(1)

In step 01, compounds A, B, C, and malononitrile can be directly purchased from the market or prepared by the conventional synthetic methods. The structures of compounds A, B and C are basically identical with the quinoid thiophene organic photoelectric material described above. It should be noted that, An can be methyl, butyl, tert-butyl or $C_1$-$C_4$ alkyl.

In step 02, the catalyst of the Stille coupling reaction is organic palladium catalyst, for example, $Pd_2(dba)_3$/P(o-Tol)$_3$, Pd(PPh$_3$)$_4$ or Pd(PPh$_3$)$_2$Cl$_2$, etc., and preferably $Pd_2$(dba)$_3$/P(o-Tol)$_3$. The solvent is tetrahydrofuran, methylene chloride, ethylene glycol dimethyl ether, benzene or toluene, and preferably tetrahydrofuran. The amount of compounds A, B, C can be calculated in accordance with the stoichiometry, or the amount of compounds A and B can be 1%~20% excess of the molar weight, which is not limited to this. The reaction is showed as the following scheme:

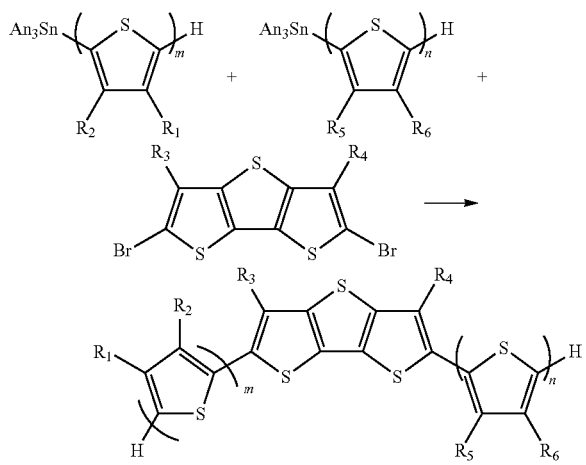

The specific implementation process of the step 02 is described as followed: under nitrogen atmosphere, anhydrous THF was added to the pressure pipe, compounds A and B and compound C were rapidly added, organic palladium catalyst was added after bubbled for tens of minutes, the pressure pipe was sealed, and the system was heated to 80° C. and refluxed for 24 hours. After completion of the reaction, purification steps are carried out as follows: KF (1.00 M) aqueous solution was added to the reaction products, stirred for tens of minutes, saturated sodium chloride solution was added, extracted by ethyl acetate, dried by anhydrous magnesium sulfate, rotary evaporation, and product was separated by silica gel column chromatography.

In Stille coupling reaction, when m≠n, in theory, compounds A and B will react with compound C, and generate compounds having (2m+2) and (2n+2) thiophene rings, respectively. In this case, the target product yield of the above reaction is low, and can be obtained by the above purification steps. It is understandable that, at this time, compounds having (2m+2) or (2n+2) thiophene rings can be purified as a quinoid thiophene organic optoelectronic materials, and belong to the protection structure of the present disclosure. When m=n, compounds A and B are identical, the target product yield is higher.

In step 03, the solvent is dimethylformamide(DMF), tetrahydrofuran, carbon tetrachloride, chloroform, methylene chloride or acetonitrile, etc., and N-bromosuccinimide (NBS), Br$_2$, HBr, or PBr$_3$ is adopted, preferably NBS. The reaction is showed as the following scheme:

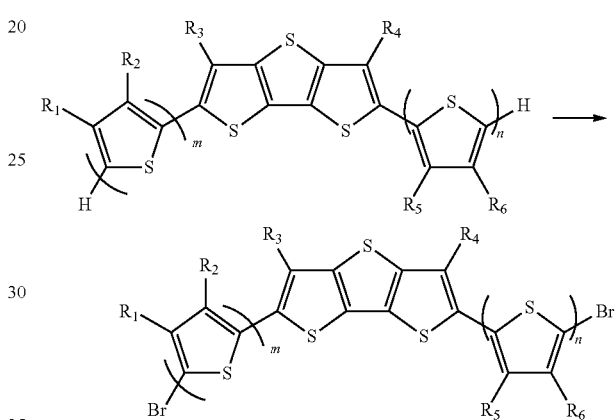

The specific implementation process is described as follow: in conditions of ice bath and dark, NBS was added in batches to a reaction vessel containing 2,6-bis(thiophene-2-yl)-dithieno[3,2-b:2',3'-d]thiophene and DMF, stirred at room temperature for 12 hours. After completion of the reaction, the reaction mixture was poured into ice water to quench, extracted by chloroform, dried by anhydrous magnesium sulfate, rotary evaporation, and product was separated by silica gel column chromatography.

In step 04, the catalyst is organic palladium catalyst, for example, Pd$_2$(dba)$_3$/P(o-Tol)$_3$, Pd(PPh$_3$)$_4$ or Pd(PPh$_3$)$_2$Cl$_2$, etc., and preferably Pd$_2$(dba)$_3$/P(o-Tol)$_3$. The solvent is glycol dimethyl ether, ethanol, methanol, dichloromethane, chloroform, tetrahydrofuran, ethyl acetate, DMF, toluene or acetone, and preferably glycol dimethyl ether. The condensing agent is sodium hydride or sodium alkoxide, and sodium alkoxide can be such as sodium methoxide or tert-butyl alcohol sodium, etc. The reaction is showed as the following scheme:

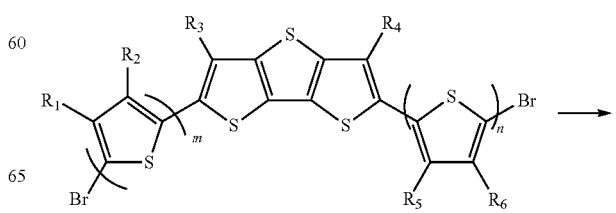

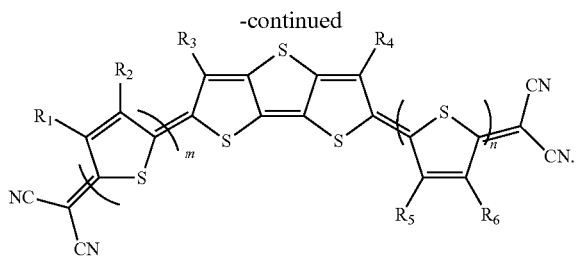

The specific implementation process is described as follow: in conditions of the ice bath, malononitrile was added to suspension containing sodium hydride (60% in oil) and ethylene glycol dimethyl ether (referred hereafter as DME), restored to room temperature, stirred for 30 minutes, the product of bromide substitution reaction and organic palladium catalyst were added to the system, heated to reflux 12 hours, cooled to 0, saturated $Br_2/H_2O$ solution and water were added to the system in turn, pumping filtrated, washed, dried, and the product was separated by silica gel column chromatography.

In the preparation method of quinoid thiophene organic photoelectric material described above, synthesis route of monomer of compounds A, B, and C is relatively simple and mature, which can reduce costs of process and manufacturing. Stille coupling reaction is a mature polymerization, which has high yield and mild conditions, and is easy to control, and solubility of the product is increased by introducing alkyl or alkoxy, and processing properties of the material is expanded.

The quinoid thiophene organic photoelectric material according to the embodiment of the present disclosure can be used in various optical or semiconductor devices, for example, it can be used in solar cell devices, organic field-effect transistors, organic electroluminescent devices, organic optical memory, non-linear organic materials and organic laser devices, etc. Solar cell devices, organic field-effect transistors and organic light-emitting devices are described as examples, as follows. Others, such as organic light memory devices, organic nonlinear materials and organic laser device are similar, and the quinoid thiophene organic optoelectronic materials according to the embodiment of the present disclosure is used for optical storage materials, nonlinear materials, laser materials or semiconductor materials and so on.

Figure 3:
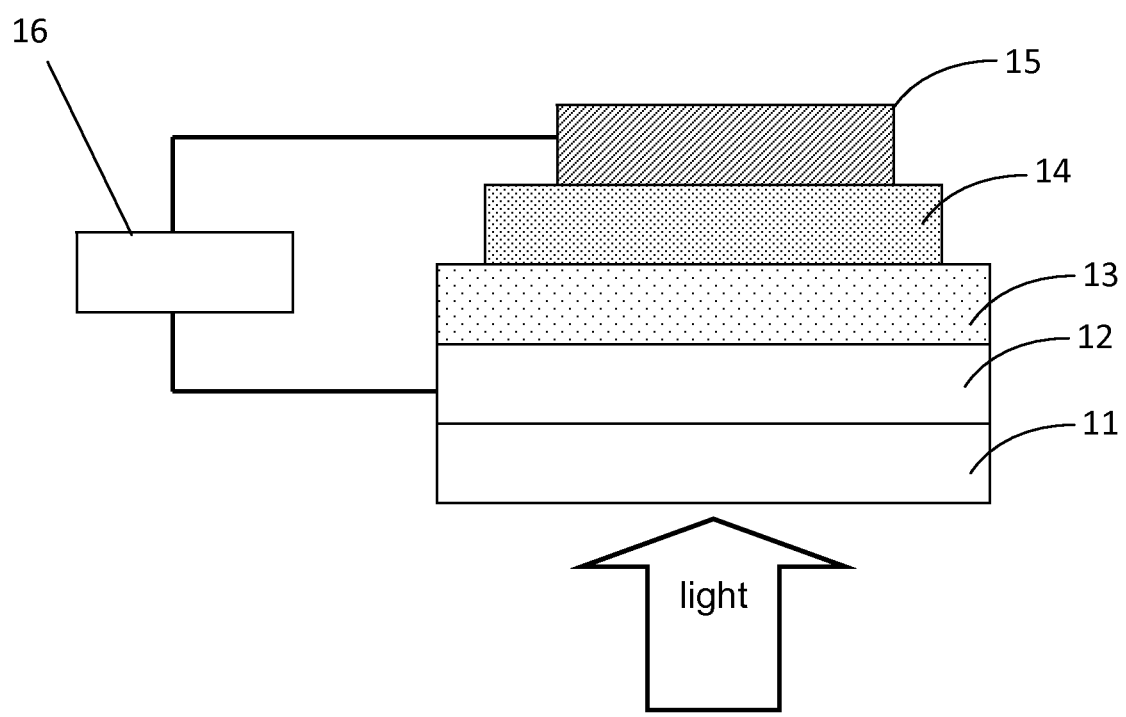
FIG. 3 is a schematic view of a solar cell device using quinoid thiophene organic photoelectric material according to an embodiment of the present disclosure.

Referring to FIG. 3, a solar cell device using quinoid thiophene organic photoelectric material the embodiment described above includes a glass substrate 11, a transparent anode 12, a middle auxiliary layer 13, an active layer 14, and a cathode 15, which are laminated in this order. The middle auxiliary layer 13 is made of a composite material of Poly(3, 4-ethylenedioxythiophene): poly(styrenesulfonate) (PEDOT:PSS). The active layer 14 includes electron donor materials and electron acceptor materials; the electron donor material is the quinoid thiophene organic photoelectric material described above; the electron acceptor material may be [6,6]-phenyl-C61-butyric acid methyl ester (PCBM). The transparent anode 12 may be indium tin oxide (ITO), preferably ITO having a sheet resistance of 10~20Ω/□. The cathode 15 may be aluminum electrodes. The glass substrate 11 may be the base, in preparation, ITO was formed on the glass substrate 11, and then the middle auxiliary layer 13 was coated on the ITO glass using oxygen-plasma spray technique. Then the quinoid thiophene organic photoelectric material and the electron acceptor material were deposited on the middle auxiliary layer 13 via vacuum evaporation to form the active layer 14. Next, the cathode 15 was deposited on the active layer 14 by vacuum evaporation technology, and the solar cell device was obtained.

As illustrated in FIG. 3, when the solar cell device is irradiated, the light goes through the glass substrate 11 and the ITO electrode 12, the quinoid thiophene organic photoelectric material in the active layer 14 absorbs solar energy and forms exciton. The exciton will be migrated to the interface between the electron donor materials and the electron acceptor materials, and electrons are transferred to the electron acceptor material, such as PCBM, such that the separation of the charge is realized, and the free carriers, i.e. free electrons and holes, are formed. The free electrons are passed to the metal cathode along the electron acceptor material and are collected by the cathode; the free holes is passed to the ITO anode along the electron donor materials and is collected by the anode, such that the photocurrent and photovoltage are formed and photoelectric conversion is achieved. When the ITO electrode 12 and the cathode 15 are connected with a load 16, the load 16 may be supplied. During the process, because of wide spectral response range of the quinoid thiophene organic photoelectric material, solar energy can be more fully used in order to obtain a higher photoelectric conversion efficiency, and increase the capacity of the electricity production of solar cell devices. Furthermore this type of organic material can reduce the weight of solar cell devices, and can be produced by technologies such as spin coating, thus facilitating the large-scale production.

Figure 4:
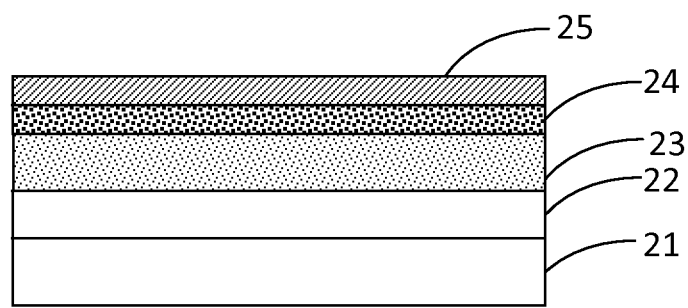
FIG. 4 a schematic view of an organic electroluminescent device using quinoid thiophene organic photoelectric material according to an embodiment of the present disclosure.

Referring to FIG. 4, an organic electroluminescent device using quinoid thiophene organic photoelectric material according to the embodiment described above includes a glass substrate 21, a transparent anode 22, a light-emitting layer 23, a buffer layer 24, and a cathode 25, which are laminated in this order. The transparent anode 22 may be indium tin oxide (ITO), preferably ITO having a sheet resistance of 10~20Ω/□. The light-emitting layer 23 contains the quinoid thiophene organic photoelectric material. The buffer layer 24 may be made of, but not limited to LiF, etc. The cathode 25 may be but not limited to aluminum electrodes or barium electrode. Therefore, in a specific embodiment, the organic electroluminescent device can be represented by ITO/quinoid thiophene organic photoelectric material/LiF/Al. The various layers described above can be formed by conventional methods, and the quinoid thiophene organic photoelectric material can be spin coated on the ITO.

Figure 5:
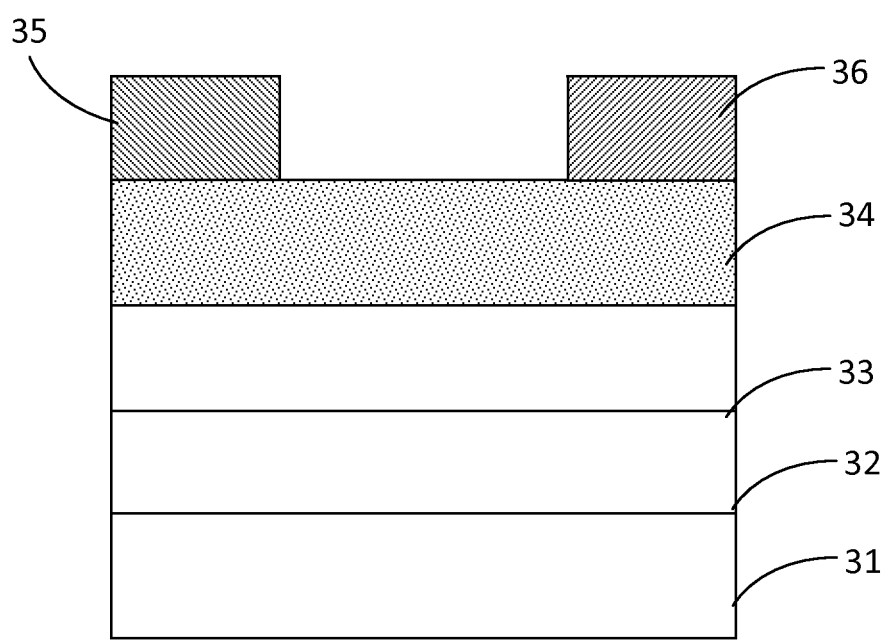
FIG. 5 a schematic view of an organic field-effect transistor using quinoid thiophene organic photoelectric material according to an embodiment of the present disclosure.

Referring to FIG. 5, an organic field-effect transistor using quinoid thiophene organic photoelectric material according to the embodiment described above includes a substrate 31, an insulation layer 32, a modified layer 33, an organic semiconductor layer 34, which are laminated in this order, and a source electrode 35 and a drain electrode 36 formed on the organic semiconductor layer 34. The substrate 31 may be, but not limited to high-doped silicon (Si); the insulation layer 32 may be, but not limited to $SiO_2$ having a micro-nm (e.g. 450 nm) thickness. The organic semiconductor layer 34 may be the quinoid thiophene organic photoelectric material. The source electrode 35 and the drain electrode 36 are made of, but not limited to gold. The modified layer 33 may be but not limited to octadecyltrichlorosilane. The substrate 31, the insulation layer 32, the modified layer 33, the source electrode 35, and the drain electrode 36 can be formed by conventional methods. The organic semiconductor layer 34 may be formed by spin coating the quinoid thiophene organic photoelectric material to the insulation layer 32 modified by the modified layer 33.

The following examples are provided for illustrate certain aspects of the preparation method of the quinoid thiophene organic photoelectric material and its performance. The raw materials used in the following embodiments can be prepared by the conventional synthesis methods, for example, dithieno [3,2-b:2',3'-d]thiophene can be prepared by 2,3-dibromothiophene after a two-step reaction, detailed preparation process can be referred by: 《Tetrahedron Letters》2002, 43, 1553; 2,2'-dithiophene can be prepared by 2-bromothiophene after a two-step reaction, detailed preparation process can be referred by: 《J. Am. Chem. Soc.》1997, 119, 12568.

Embodiment 1

The quinoid thiophene organic photoelectric material of embodiment 1 is represented by the following formula:

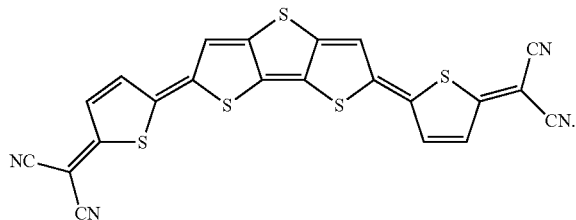 [SMILES: N#CC(C#N)=c1cc/c(=c2\cc3sc4c/c(=c5/ccc(=C(C#N)C#N)s5)sc4c3s2)s1]

The structure shows that, the quinoid thiophene organic optoelectronic material has a symmetric structure, which has four quinoid thiophene ring and two pairs of cyano. $R_1$, $R_2$, $R_3$, $R_4$, $R_5$ and $R_6$ are all H, m=n=1, cyano is electron withdrawing groups, such symmetrical structure makes the quinoid thiophene organic optoelectronic materials has a relatively good light absorption performance and optical performance, and small molecular weight, products made from has lighter weight.

The specific implementation process of the preparation of quinoid thiophene organic photoelectric material according to embodiment 1 is described as follow:

1) 2,6-dibromo-dithieno[3,2-b:2',3'-d]thiophene was prepared, which is the compound C of the embodiment, represented by the following formula:

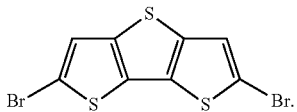

The specific implementation process is described as follow: in conditions of ice bath and dark, 39.16 g NBS was added to a reaction flask containing 19.6 g dithieno[3,2-b:2',3'-d]thiophene and 200 mL DMF, the mixture was stirred at room temperature for 12 hours. After completion of the reaction, the reaction mixture was poured into ice water to quench, extracted by chloroform, dried by anhydrous magnesium sulfate, rotary evaporation, and product was separated by silica gel column chromatography.

Test results were: MALDI-TOF-MS (m/z): 354.1 (M+).

2) tributyltin-(thiophene-2-yl) tin was prepared, which is the compound A or B of the embodiment, represented by the following formula:

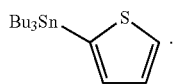

In this step, compounds A and B have the same structure, and thus compounds A and B can be prepared by step 2) once, which can simplify the preparation process and reduce costs.

On the contrary, if the structure of the quinoid thiophene organic photovoltaic material is not symmetrical, the compounds A and B have different structures, compounds A and B need to be prepared by step 2) with different raw materials, respectively.

The specific implementation process is described as follow: 8.4 g thiophene and 100 mL anhydrous THF solution were added to a reaction vessel, and 34.5 mL butyl lithium solution (2.9 M hexane solution) was added in drops. After stirred for 1 hour, 32.5 mL tributyltin chloride was added in drops, and the mixture was continue stirred for 4 hours. After completion of the reaction, the reaction mixture was recovered to room temperature, saturated ammonium chloride aqueous solution was added, extracted by dichloromethane, dried by anhydrous magnesium sulfate, rotary evaporation, and product was separated by silica gel column chromatography. Purification was not required at the end of this step, and the next step can be directly proceeded.

3) 2,6-bis(thiophene-2-yl)-dithieno[3,2-b:2',3'-d]thiophene is prepared, represented by the following formula:

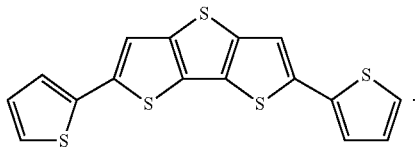 [SMILES: c1csc(-c2cc3sc4cc(-c5cccs5)sc4c3s2)c1 ; "."]

This step is the step 2 described above. In this step, compounds A and B have the same structure, therefore, on the one hand, it simplifies the source of raw materials, which also simplifies the fabrication process and reduce costs. On the other hand, this step has a higher yield relative to the use of different compounds A and B.

The specific implementation process is described as follow: under nitrogen atmosphere, 40 mL anhydrous THF was added to a pressure pipe, 3.54 g 2,6-dibromo-dithieno[3,2-b:2',3'-d]thiophene and 8.21 g tributyltin-(thiophene-2-yl) tin were rapidly added, 0.18 g $Pd_2(dba)_3$ and 0.12 g $P(o-Tol)_3$ were added after bubbled for tens of minutes, the pressure pipe was sealed, and the system was heated to 80° C. and refluxed for 24 hours. After completion of the reaction, 10 mL KF (1.00 M) aqueous solution was added to the reaction products, stirred for thirty minutes, saturated sodium chloride solution was added, extracted by ethyl acetate, dried by anhydrous magnesium sulfate, rotary evaporation, and product was separated by silica gel column chromatography.

Test results were: MALDI-TOF-MS (m/z): 360.6 (M+).

4) 2,6-bis(5-bromo-thiophene-2-yl)-dithieno[3,2-b:2',3'-d]thiophene was prepared, represented by the following formula:

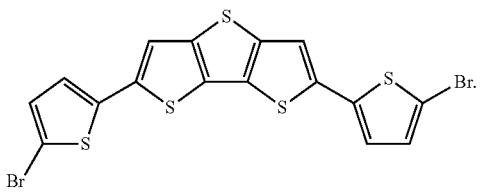 [SMILES: Brc1ccc(-c2cc3sc4cc(-c5ccc(Br)s5)sc4c3s2)s1]

The specific implementation process is described as follow: in conditions of ice bath and dark, 1.8 g NBS was added to a reaction flask containing 1.8 g 2,6-bis(thiophene-2-yl)-dithieno[3,2-b:2',3'-d]thiophene and 30 mL DMF, stirred at room temperature for 12 hours. After completion of the reaction, the reaction mixture was poured into ice water to quench, extracted by chloroform, dried by anhydrous magnesium sulfate, rotary evaporation, and product was separated by silica gel column chromatography.

Test results were: MALDI-TOF-MS (m/z): 518.4 ($M^+$).

5) The final product was prepared, represented by the formula described above.

The specific implementation process is described as follow: in conditions of the ice bath, 0.17 g malononitrile was added to a suspension containing 0.22 g sodium hydride (60% in oil) and 20 mL ethylene glycol dimethyl ether, the mixture was restored to room temperature, stirred for 30 minutes, 0.56 g 2,6-bis(5-bromo-thiophene-2-yl)-dithieno[3,2-b:2',3'-d]thiophene and 0.074 g $PdCl_2(PPh_3)_2$ were added to the system, heated and refluxed for 12 hours, cooled to 0, 20 mL saturated $Br_2/H_2O$ solution was added to the system. Water was added to the system, pumping filtrated, washed, dried, and the product was separated by silica gel column chromatography, the yield of the product is 65%.

Test results were: MALDI-TOF-MS (m/z): 488.7 ($M^+$).

Embodiment 2

The quinoid thiophene organic photoelectric material of embodiment 2 is represented by the following formula:

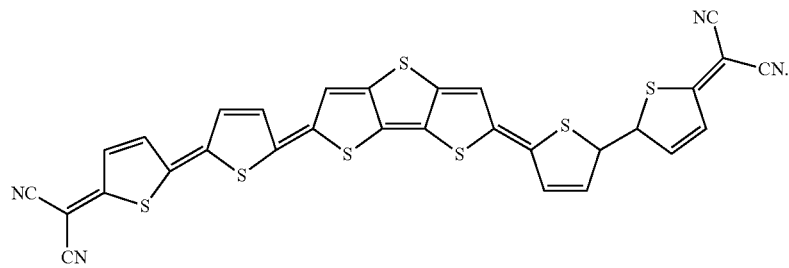 [SMILES: N#CC(C#N)=C1C=CC(C2C=C/C(=c3/cc4sc5c/c(=c6\cc/c(=c7\ccc(=C(C#N)C#N)s7)s6)sc5c4s3)S2)S1]

The structure of the quinoid thiophene organic photoelectric material is similar to the structure of embodiment 1, and of which has symmetrical structure. $R_1$, $R_2$, $R_3$, $R_4$, $R_5$ and $R_6$ are all H, the difference is that the quinoid thiophene organic photoelectric material of embodiment 2 has six quinoid thiophene ring, and m=n=2. cyano is electron withdrawing groups, such symmetrical structure makes the quinoid thiophene organic optoelectronic materials has a relatively good light absorption performance and optical performance.

The specific implementation process of the preparation of quinoid thiophene organic photoelectric material according to embodiment 2 is described as follow:

1) 2,6-dibromo-dithieno[3,2-b:2',3'-d]thiophene was prepared, which is the compound C of the embodiment 1, specific implementation process of which is the same with the step 1) of embodiment 1, and is need not to repeat.

2) 5-tributyltin chloride-2,2'-dithiophene was prepared, which is the compound A or B, represented by the following formula:

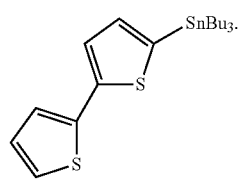

It is the same with embodiment 1 that the compounds A and B have the same structure, and thus the compounds A and B can be prepared by step 2) once, which simplifies the preparation process and reduces costs. On the contrary, if the structure of the quinoid thiophene organic photovoltaic material is not symmetrical, the compounds A and B have different structures, compounds A and B need to be prepared by step 2) with different raw materials, respectively.

The specific implementation process is described as follow: 16.6 g 2,2'-dithiophene and 120 mL anhydrous THF solution were added to a reaction vessel, and 34 mL butyl lithium solution (2.9 M hexane solution) was added in drops. After stirred for 1 hour, 33 mL tributyltin chloride was added in drops, and the mixture was continue stirred for 6 hours. After completion of the reaction, the reaction mixture was recovered to room temperature, saturated ammonium chloride aqueous solution was add, extracted by dichloromethane, dried by anhydrous magnesium sulfate, rotary evaporation, and product was separated by silica gel column. Purification was not required at the end of this step, and the next step can be directly proceeded.

3) 2,6-bis(2,2'-dithiophene-5-yl)-dithieno[3,2-b:2',3'-d]thiophene was prepared, represented by the following formula:

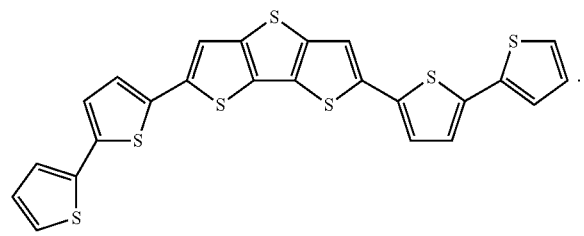 [SMILES: c1csc(-c2ccc(-c3cc4sc5cc(-c6ccc(-c7cccs7)s6)sc5c4s3)s2)c1 ; "."]

It is the same with embodiment 1 that the compounds A and B have the same structure, therefore, on the one hand, it simplifies the source of raw materials, which also simplifies the fabrication process and reduces costs. On the other hand, this step has a higher yield relative according to the use of different compounds A and B.

The specific implementation process is described as follow: under nitrogen atmosphere, 80 mL anhydrous THF was added to a pressure pipe, 7.08 g 2,6-dibromo-dithieno[3,2-b:2',3'-d]thiophene and 20.05 g 5,5'-bis-tributyltin chloride-2,2'-dithiophene were rapidly added, 0.4 g $Pd_2(dba)_3$ and 0.26 g $P(o-Tol)_3$ were added after bubbled for thirty minutes, the pressure pipe was sealed, and the system was heated to 80° C. and refluxed for 24 hours. After completion of the reaction, 20 mL KF (1.00 M) aqueous solution was added to the reaction products, stirred for forty minutes, saturated sodium chloride solution was added, extracted by ethyl acetate, dried by anhydrous magnesium sulfate, rotary evaporation, and product was separated by silica gel column chromatography.

Test results were: MALDI-TOF-MS (m/z): 524.8 ($M^+$).

4) 2,6-bis(5'-bromo-2,2'-dithiophene-5-yl)-dithieno[3,2-b:2',3'-d]thiophene was prepared, represented by the following formula:

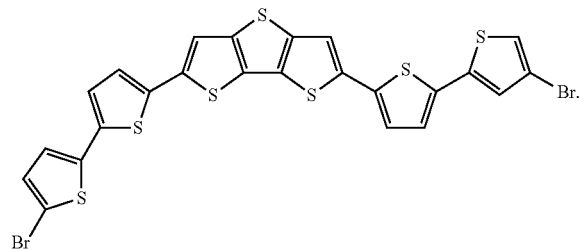 [SMILES: Brc1csc(-c2ccc(-c3cc4sc5cc(-c6ccc(-c7ccc(Br)s7)s6)sc5c4s3)s2)c1]

The specific implementation process is described as follow: in conditions of ice bath and dark, 3.92 g NBS was added to the reaction flask containing 5.25 g 2,6-bis(2,2'-dithiophene-5-yl)-dithieno[3,2-b:2',3'-d]thiophene and 40 mL DMF, stirred at room temperature for 10 hours. After completion of the reaction, the reaction mixture was poured into ice water to quench, extracted by chloroform, dried by anhydrous magnesium sulfate, rotary evaporation, and product was separated by silica gel column chromatography.

Test results were: MALDI-TOF-MS (m/z): 682.7 ($M^+$).

5) The final product was prepared, represented by the formula described above.

The specific implementation process is described as follow: in conditions of ice bath, 0.37 g malononitrile was added to suspension containing 0.48 g sodium hydride (60% in oil) and 30 mL ethylene glycol dimethyl ether, recovered to room temperature, stirred for 30 minutes, 1.47 g 2,6-bis(5'-bromo-2,2'-dithiophene-5-yl)-dithieno[3,2-b:2',3'-d]thiophene and 0.16 g $PdCl_2(PPh_3)_2$ were added to the system, heated and refluxed for 12 hours, cooled to 0° C., saturated $Br_2/H_2O$ solution was added to the system. Water was added to the system, pumping filtrated, washed, dried, and the product was separated by silica gel column chromatography, the yield of the product is 62%.

Test results were: MALDI-TOF-MS (m/z): 650.9 ($M^+$).

It can know from the above, the quinoid thiophene organic photoelectric material has a plurality of thiophene rings with quinoid structures, and the thiophene ring is five-membered ring structure which complies with Huckel rule, having moderate energy bandgap, wide spectral response, good thermal stability and environmental stability. Moreover, the quinoid thiophene organic photoelectric material described above has strong electron withdrawing groups cyano vinyl (=$C(CN)_2$) at both ends of the molecular chain, that make it become quinoid thiophene containing dithiophene and thiophene unit, further widening the range of the material on the absorption of the solar spectrum, for example, the absorption band edge of material is pushed to the red and near infrared region, to improve the optical and electrical properties of the material and the photoelectric conversion efficiency of the material. In the preparation method of quinoid thiophene organic photoelectric material described above, the use of relatively simple synthetic route and Stille coupling reactions simplifies the process and reduces manufacturing costs. While the quinoid thiophene organic photoelectric material described above is used in solar cell devices, organic field-effect transistors and organic electroluminescent devices, organic optical memory, non-linear organic materials or organic laser devices, their the optical or semiconductor-related performance can be improved, their quality can be reduced, and it can facilitate the preparation of large quantities.

It should be understood that the embodiments described above are only to explain the present disclosure, not used to limit the present disclosure. Rather, the specific features and acts are disclosed as sample forms of implementing the claimed invention.

What is claimed is:

1. A quinoid thiophene organic photoelectric material, comprising the compound represented by the following formula (1):

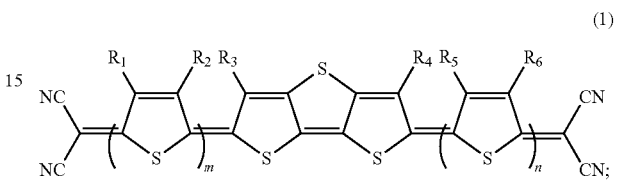

wherein $R_1$, $R_2$, $R_3$, $R_4$, $R_5$ and $R_6$, which are identical or different, represent H or $C_1$~$C_{30}$ alkyl or alkoxy, m and n, which are identical or different, represent integers between 1 and 20.

2. The quinoid thiophene organic photoelectric material according to claim 1, wherein $R_1$ and $R_6$ are identical H or $C_1$~$C_{30}$ alkyl or alkoxy, $R_2$ and $R_5$ are identical H or $C_1$~$C_{30}$ alkyl or alkoxy.

3. The quinoid thiophene organic photoelectric material according to claim 1, wherein m and n are integers between 1 and 20.

4. The quinoid thiophene organic photoelectric material according to claim 1, wherein m and n are identical, and represent 1 or 2.

5. A preparation method of quinoid thiophene organic photoelectric material, comprising:
providing compounds A, B, C represented by the following formulas and malononitrile, respectively,

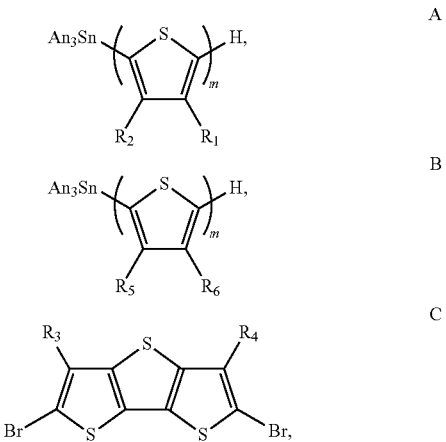

wherein $R_1$, $R_2$, $R_3$, $R_4$, $R_5$ and $R_6$, which are identical or different, represent H or $C_1$~$C_{30}$ alkyl or alkoxy, m and n, which are identical or different, represent integers between 1 and 20, An represents $C_1$~$C_4$ alkyl;
processing compounds A, B, and C by Stille coupling reaction in the presence of a catalyst and a solvent;
processing the product of Stille coupling reaction by bromide substitution reaction to obtain a product of bromide substitution reaction;

processing the product of bromide substitution reaction and malononitrile by condensation reaction in the presence of a catalyst, a condensing agent and a solvent to obtain the compound represented by the following formula (1):

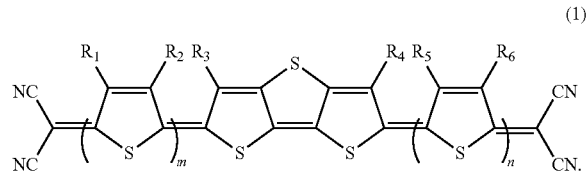

(1)

6. The preparation method of quinoid thiophene organic photoelectric material according to claim 5, further comprising:
separating and purifying the product of Stille coupling reaction, the product of bromide substitution reaction, and the product of condensation reaction respectively by silica gel column chromatography to obtain the corresponding product of Stille coupling reaction, the corresponding product of bromide substitution reaction, and the corresponding compounds represented by the formula (1).

7. The preparation method of quinoid thiophene organic photoelectric material according to claim 5, wherein the bromide substitution reaction comprises: processing the product of Stille coupling reaction and N-bromosuccinimide, $Br_2$, HBr, or $PBr_3$ by bromide substitution reaction in the presence of solvent of dimethylformamide, tetrahydrofuran, carbon tetrachloride, chloroform, methylene chloride or acetonitrile.

8. The preparation method of quinoid thiophene organic photoelectric material according to claim 5, wherein the catalyst of condensation reaction is organic palladium catalyst; the solvent of condensation reaction is glycol dimethyl ether, ethanol, methanol, dichloromethane, chloroform, tetrahydrofuran, ethyl acetate, DMF, toluene or acetone.

9. The preparation method of quinoid thiophene organic photoelectric material according to claim 5, wherein the catalyst of the Stille coupling reaction is organic palladium catalyst; the solvent of Stille coupling reaction is tetrahydrofuran, methylene chloride, ethylene glycol dimethyl ether, benzene or toluene; the condensing agent is sodium hydride or sodium alkoxide.

10. A method for the applications of the quinoid thiophene organic photoelectric material according to claim 1 in manufacture of solar cell devices, organic field-effect transistors, organic electroluminescent devices, organic optical memory, non-linear organic materials or organic laser devices.

11. A method for the applications of the quinoid thiophene organic photoelectric material according to claim 2 in manufacture of solar cell devices, organic field-effect transistors, organic electroluminescent devices, organic optical memory, non-linear organic materials or organic laser devices.

12. A method for the applications of the quinoid thiophene organic photoelectric material according to claim 3 in manufacture of solar cell devices, organic field-effect transistors, organic electroluminescent devices, organic optical memory, non-linear organic materials or organic laser devices.

13. A method for the applications of the quinoid thiophene organic photoelectric material according to claim 4 in manufacture of solar cell devices, organic field-effect transistors, organic electroluminescent devices, organic optical memory, non-linear organic materials or organic laser devices.

* * * * *